United States Patent
Weber

(12)
(10) Patent No.: US 6,344,038 B1
(45) Date of Patent: Feb. 5, 2002

(54) SURGICAL ANTI-FRICTION DEVICE

(76) Inventor: Paul J. Weber, 1 Seneca Rd., Ft. Lauderdale, FL (US) 33308

( * ) Notice: Subject to any disclaimer, the term of this patent is extended or adjusted under 35 U.S.C. 154(b) by 0 days.

(21) Appl. No.: 09/630,249

(22) Filed: Aug. 1, 2000

Related U.S. Application Data

(63) Continuation-in-part of application No. 09/203,413, filed on Dec. 2, 1998, now Pat. No. 6,120,519.

(51) Int. Cl.[7] .............................................. A61B 17/00
(52) U.S. Cl. ........................... 606/1; 604/147; 604/175; 604/164.04
(58) Field of Search ................................ 606/170–171, 606/1; 604/176, 240, 272, 164.04, 175, 174; 241/95

(56) References Cited

U.S. PATENT DOCUMENTS

| | | | |
|---|---|---|---|
| 3,308,819 A | * | 3/1967 | Arp |
| 4,925,450 A | * | 5/1990 | Imonti et al. ................ 604/240 |
| 5,226,890 A | * | 7/1993 | Ianniruberto et al. ........ 604/164 |
| 5,295,980 A | * | 3/1994 | Ersek .......................... 604/272 |
| 5,400,768 A | * | 3/1995 | McNamara et al. ......... 606/170 |
| 5,632,124 A | * | 5/1997 | Weingarten et al. ........... 52/187 |
| 5,782,813 A | * | 7/1998 | Yoon ........................... 604/174 |
| 5,817,062 A | * | 10/1998 | Flom et al. .................. 604/174 |
| 5,984,896 A | * | 11/1999 | Boyd ........................... 604/175 |
| 6,044,599 A | * | 4/2000 | Wachenfeld .................. 52/187 |

* cited by examiner

*Primary Examiner*—Michael H. Thaler
(74) *Attorney, Agent, or Firm*—L. E. Carnahan

(57) ABSTRACT

A surgical anti-friction device for use with highly flexible, reinforced swan neck liposuction cannulas. The flexible cannulas are constructed of metal and plastic, with the metal cannulas having diameters of between 2.0 and 3.5 mm, and with the plastic cannulas having diameters greater than 3.5 mm (i.e., 3.5 to 6.0 mm), and are inserted through the surgical anti-friction device. These long shaft flexible cannulas, when utilized in combination with a reinforced neck, allow the cannula point of entry to act as a fulcrum (with an optional interposed insert) in concert with the surgeon's guiding hand to deflect the cannulas. The surgical anti-friction device protects the incision through which the cannula passes. The long, flexible plastic cannula shafts are provided central metal "memory" reinforcing wires of varying thicknesses along the length thereof which allow controlled rigidity of the long plastic shafts, and enable the cannulas to be bent into a semi-circle without breaking and yet return to their original shape. The surgical anti-friction device or insert is configured, for example, as a cone with rows of V-shaped cuts on the surface. The V-shaped cuts may extend in opposite directions to define a space or blank area therebetween, which may be located adjacent the skin area when inserted into an incision or opening, and functions to prevent movement of the insert in either direction.

9 Claims, 4 Drawing Sheets

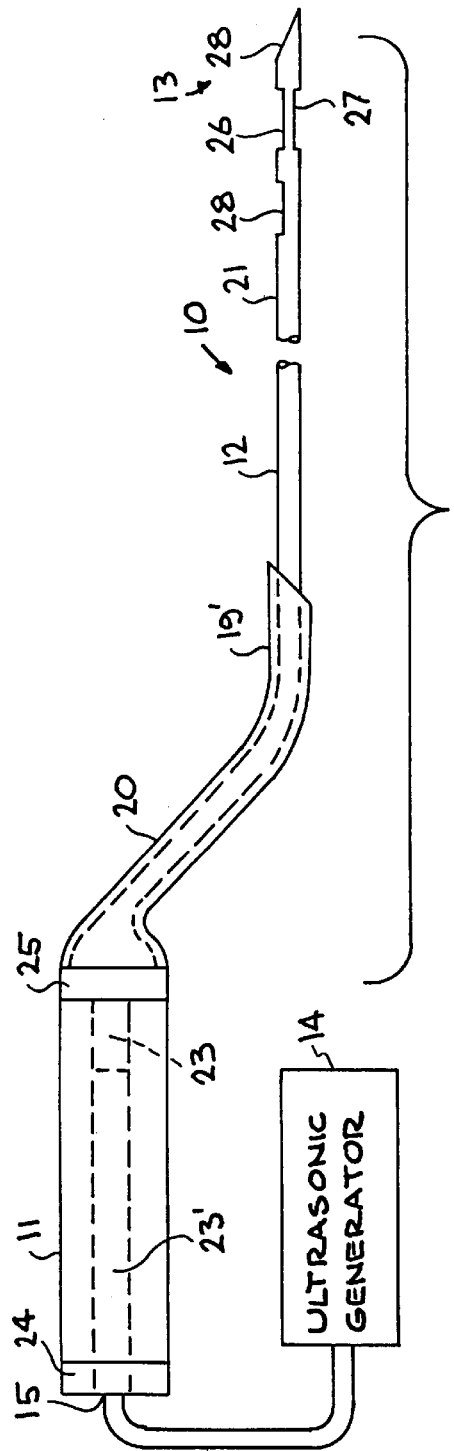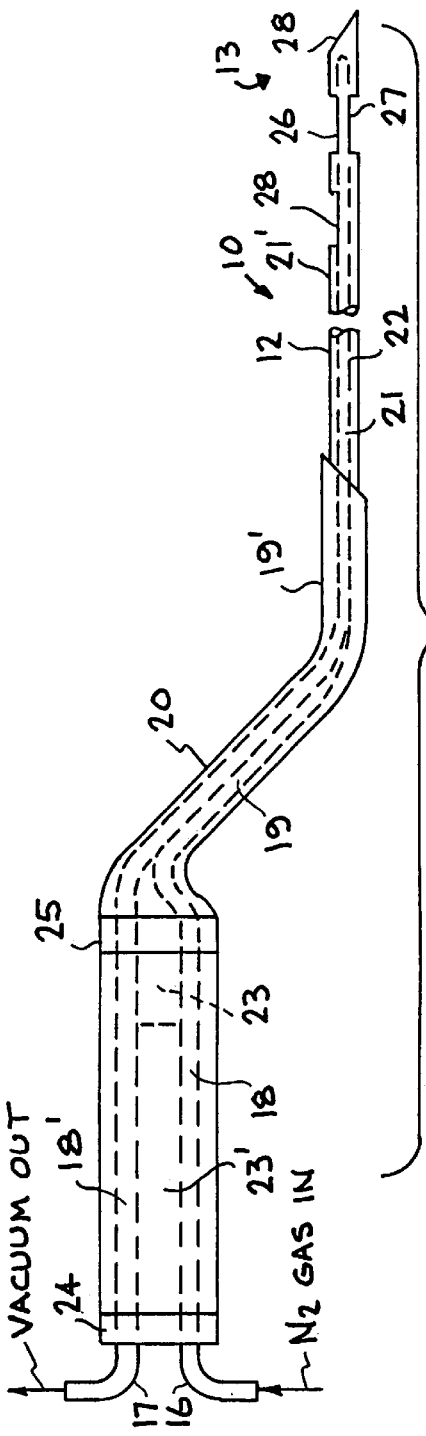

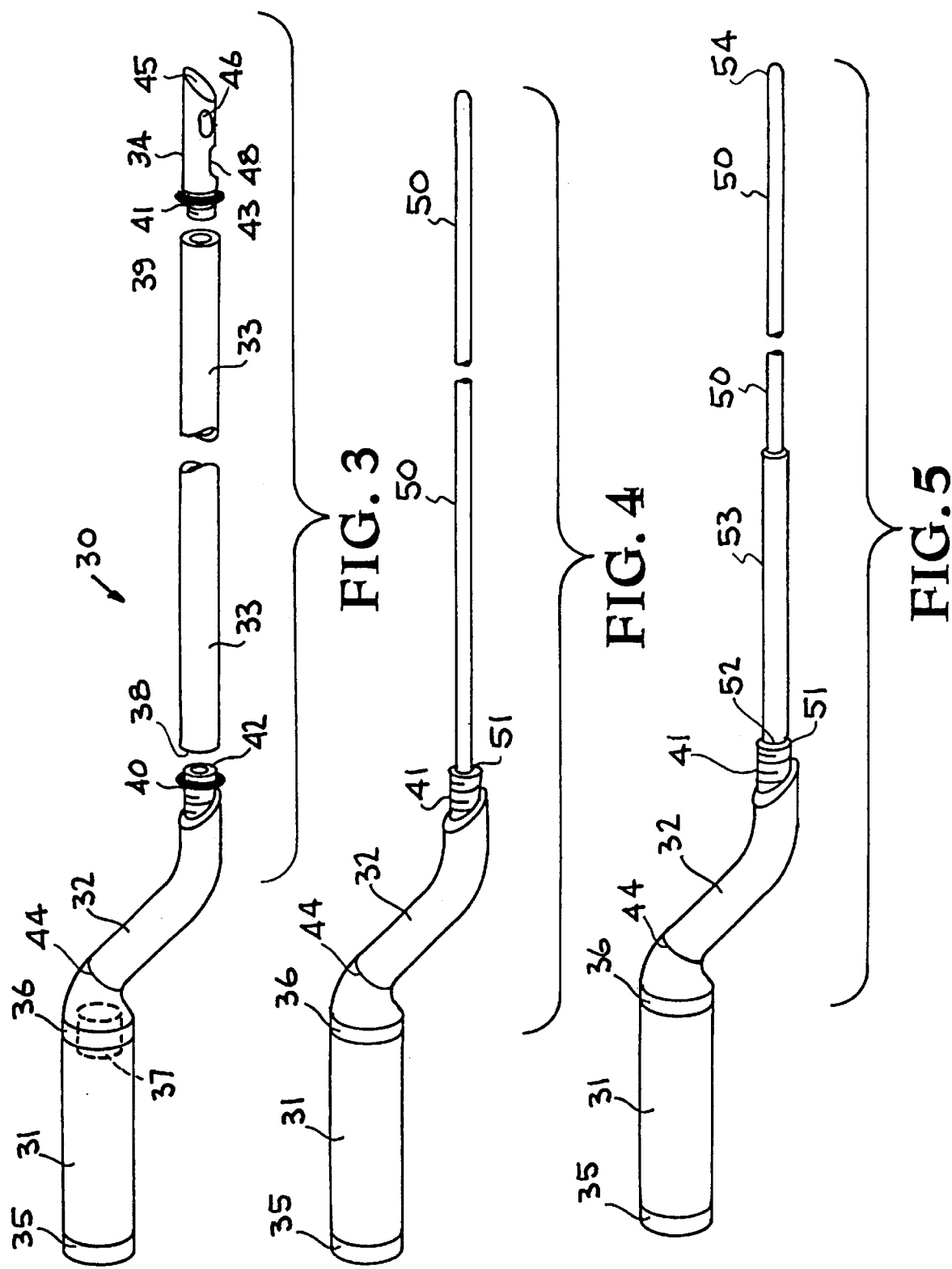

SURGICAL ANTI-FRICTION DEVICE

RELATED APPLICATION

This application is a continuation-in-part of U.S. application Ser. No. 09/203,413 filed Dec. 2, 1998 now U.S. Pat. No. 6,120,519.

BACKGROUND OF THE INVENTION

The present invention relates to a surgical device, particularly to surgical devices for use with liposuction cannula shafts, and more particularly to a surgical anti-friction incision insert or device through which surgical tools, such as cannula shafts, pass into an interior of a body and are retained in the incision by friction members on the external areas of the device.

Liposuction, which literally means "fat suction", is a technique that pulls fat out of the body by means of teasing, pulling, scraping or suction. It can be used to reduce the volume of fat in many regions of the body, but is particularly effective in areas such as thighs and abdomen which contain genetically determined fat not responsive to diet or exercise. Liposuction is currently an established modality in cosmetic surgery, performed by surgeons as an elective operation, and is one of the most common procedures in medicine.

Traditional and ultrasonic liposuction cannulas usually are relatively rigid. The relative rigidity has its advantages and disadvantages. Advantages of relative rigidity include control, ease of manufacture and propagation of ultrasonic energy. Disadvantages of the rigidity include the fact that most areas of the human body are curviform and that the combination of straightness and rigidity places undesirable forces on the tissues adjacent to the cannula tips and tissues of the entrance wounds while the cannula is inserted in the patient. An article entitled "Reinforced Swan-Neck, Flexible Shaft, Beveled Liposuction Cannulas", P. J. Weber et al, The American Journal of Cosmetic Surgery, Vol. 16, No. 1, 1999, 41–47, described the use of a stainless steel shaft system with a reinforced swan neck for shaft diameters between 2.0 and 3.5 mm and drew comparisons with the prior art. Such a reinforced swan neck/shaft system is also described and claimed in above referenced copending application Ser. No. 09/203,413 for use with sonic, ultrasonic and cooling systems. This system allows the cannula point of entry to act as a fulcrum (with an optional interposed insert) in concert with the surgeon's guiding hand to deflect cannulas with long flexible shafts and highly reinforced swan necks. The cannula tip is preferably highly beveled with an adjacent set of three openings. The system easily penetrates fibrous fat and may reach fat deposits relatively distant from the entrance wounds. The highly flexible, reinforced swan neck cannula shafts are intended to move in an easily controllable manner within the subcutaneous tissue below the dermal envelope in an arciform fashion. Benefits include a reduced need to move a patient's body position intraoperatively. A Teflon entrance wound insert (or anti-friction means), also described and claimed in copending application Ser. No. 09/203,413, provides for reduced friction and tissue trauma at the dermal-epidermal level. The surgeon may require time to become proficient at maximizing the usage of novel cannula motions that occur as a result of using the cannula entrance point as a fulcrum and redirecting the distal shaft and tip of the cannula with an opposing hand. The novel motions arise from the minimally to highly arced possible cannula paths.

Many innovative cannula types and designs have been described and manufactured. Over time, the most commonly used variations have become the basis of traditional liposuction cannula design. Cannula designs may be categorized according to tip, aperture, shaft, handle, alloy and customization features. The cannula system described and claimed in copending application Ser. No. 09/203,413 contains a unique combination of modifications and innovations not previously known. That 2.5–3.5 mm diameter metal shaft system was originally conceived to address the needs of ballerinas, fashion models, professional cheerleaders and the like's concerns about delicate fat removal with a minimum of cannula entrance wounds. Other issues that fostered a need for the cannula system included body curvature considerations and the need for intraoperative patient movement and positioning on the table. Previous attempts to address similar needs included the use of various long, rigid but slightly curved cannulas.

Many cannula tip designs are currently available. Each design has its positive and negative dynamics or attributes under varying conditions of usage. Liposuction cannula design dynamics have been summarized in the above referenced article by P. J. Weber et al. The tri-port bevel tip of copending application Ser. No. 09/203,413 has been found to penetrate the fibrous fat with relative ease in combination with the systems herein described. Cannula passage in even the fibrous environment of previously suctioned patients appears facilitated. The tri-port bevel tip combination, although a very aggressive fat removing design, has yielded as little bleeding as we have seen with any other cannula tip design. Precise control over the aggressive action of multiple tip opening cannulas is recommended and may be gained by reducing the suction pump vacuum level to a suggested level of −12 Torr. The reinforced swan neck cannula should be moved slowly at first through the patient's tissues until the surgeon develops the necessary skills to consistently guide the cannulae to the appropriate target. Slow passage of these cannulae will usually provide aggressive liposuction and should be continuously monitored visually through the clear suction tubing and by target site palpation.

Swan neck modifications have been used in the past to aid the surgeon in directing the movement and placement of the cannula in close areas. Nonetheless, the forces customarily generated by the surgeon's arm during the course of surgery have been known to cause premature breakage in previous swan neck design junctions. Problems with earlier swan necks have included localized metal weakness, fracture, failure, undesired "bendability" and awkwardness. More positively, the reinforced swan neck of copending application Ser. No. 09/203,413 provides a previously unattainable example that can now more fully demonstrate the many benefits of swan neck systems. Swan neck formations are especially helpful in combination with longer cannula shafts since traditional cannula linearity, length and rigidity may contribute to increase the probability that the surgeon's hand or cannula handle will bump or strike a patient's protuberance or convexity. Without swan neck modifications, the cumbersome length and rigidity of designs of previous cannulas caused surgeons to place additional stress on their own arms and the patient's tissues to guide the cannula shaft and handle in a workable fashion. In the above referenced 2.5–3.5 mm metal shaft cannula system, the swan necks have been specially and grossly reinforced. This reinforcement provides the needed additional stability at the handle/shaft junction to help a surgeon increase leverage on the cannula shaft and thus make use of the cannula entrance point as a fulcrum. Increased shaft leverage, in turn, allows the tip of the cannula to move in both traditionally expected and novel directions. To the surgeon who is not accustomed to using the new cannulas, this change and apparent unpredictability of tip movement may be alarming. Fortunately, with practice, tip motion can be perfected and the benefits of the new cannulas will become apparent.

Factors affecting a surgeon's selection of shaft length and character may be numerous. These factors may include the following: ease of tip location detection with shorter cannulas, concerns of increased handle/shaft junction breakage with increased length secondary to length-induced leverage, the secondary need for increased shaft diameter to increase strength (durability) when a longer cannula is desired, the advantage of minimizing the number of holes by using longer cannula. The reinforced swan neck allows for an increased range of workable cannula lengths for a variety of metal shaft diameters. These attributes, together with the special tip bevel, allow controllable tissue penetration with novel motions that should reduce the number of entrance incisions, hasten the procedure, reduce the need for patient repositioning. These benefits have been attained without apparent increased bleeding or complications. The use of high memory, extended length cannulas allows for movements and attributes heretofore considered problematic. For example, unique approaches to "hard-to-reach" areas, as well as decreasing the number of entry point openings, may modify a surgeon's repertoire.

Along with the tip modification and swan neck modification changes, shaft specification alterations have been made. The longer stainless steel shafts have been successfully used in all of our liposuctions performed numerous times. Stainless steel shafts in this cannula system are 2.0, 2.5, 3.0 and 3.5 mm in diameter. Currently available stainless steel tubing does not provide the flexibility or memory needed for proper function for shaft diameters exceeding 3.5 mm. However, certain alloys may enable an increase in diameter to about 5 mm.

Although shaft diameters between 2.0 and 3.5 mm provide surprisingly efficient and aggressive liposuction, many surgeons require cannula shaft diameters exceeding 4 mm to address obese patients and larger liposuction cases. However, metal cannulas with long shafts exceeding 3.5 mm in diameter of stainless steel were found on extensive testing to not possess the desirable qualities of a wide range of flexibility in combination with proper memory. The range for metal shafts is up to about 5.0 mm, preferably about 3.5 mm.

U.S. Pat. No. 6,090,121 issued Jul. 18, 2000 to P. J. Weber et al provides a new system using plastic cannula shafts with internal memory metal support wires which satisfies the need for cannula shafts having diameters of over 3.5 mm and up to 6–7 mm diameters. This plastic/support wire system has been tested successfully. The cannula shaft memory wires allow controlled rigidity of the plastic shafts and the cannulas can be bent into a semi-circle without breaking and yet still return to the original shape due to the internal metal support wire which provides the memory for the plastic shafts. The metal support wire decreases in thickness toward the distal end and may be covered with a Teflon coating to prevent excess load heating during autoclave sterilization of the plastic shaft. Also, the reinforced swan neck is provided with a disconnect which enables ready change of shafts of different diameters. Thus, the plastic cannula shaft system of U.S. Pat. No. 6,090,121, along with the above referenced metal cannula shaft system, provides a surgeon with the tools necessary to perform the complete spectrum of various liposuction procedures.

The surgical anti-friction device of the present invention, which is an improvement over the entrance wound insert of copending application Ser. No. 09/203,413, is provided with V-shaped cuts which prevent further insertion or removal of the device or insert as well as providing an area without the V-shaped cut which is designed to be located in an area of the tissue or skin of the body in which the device is inserted.

SUMMARY OF THE INVENTION

It is an object of the present invention to provide a surgical anti-friction device for insertion into incisions.

A further object of the invention is to provide a surgical anti-friction device for use with a surgical tool, such as a liposuction device which may include a reinforced swan neck and a plastic cannula shaft.

Another object of the invention is to provide a surgical insert which has an internal anti-friction surface and an external friction surface.

Another object of the invention is to provide a surgical anti-friction device which includes at least one row of V-shaped cuts for preventing removal from an incision in a body.

Another object of the invention is to provide a surgical insert which includes at least two rows of oppositely directed V-shaped cuts for preventing movement in opposite directions.

Another object of the invention is to provide a surgical insert which includes a plurality of rows of V-shaped cuts, at least two adjacent rows having oppositely directed V-shaped cuts and being spaced apart to form an area therebetween.

Another object of the invention is to provide a surgical anti-friction device or insert which has at least one row of V-shaped cuts and configured with a tapered surface, a partially tapering surface, or a cylindrical surface.

The present invention involves a surgical insert or device which is constructed of or coated with an anti-friction material which enables unimpeded movement of a surgical tool through the device while being provided with means for preventing undesired movement of the device when inserted into an incision in a body. While the device of this invention is particularly suited for passage therethrough of a cannula shaft for liposuction procedures, the device can be configured for use with other surgical tools and thus is not limited to liposuction applications. The surgical device of this invention includes one or more rows of V-shaped cuts, which points function to prevent removal from an incision and/or further insertion of the device into the incision. The row or rows of V-shaped cuts extend around the entire outer surface of the device with the point of the V-shaped cuts extending outwardly. The rows of V-shaped cuts may extend in the same direction or in an opposite direction, or adjacent rows may be spaced apart and the V-shaped cuts extend in an opposite direction to form an area therebetween without the cuts, and which area may be designed to be in contact with the skin area of the incision.

BRIEF DESCRIPTION OF THE DRAWINGS

The accompanying drawings, which are incorporated into and form a part of the disclosure, illustrate embodiments of the invention and, together with the description, serve to explain the principles of the invention.

FIG. 1 is a side view of an embodiment of a liposuction device including a handle removably connected to a hollow, flexible cannula shaft having a high memory of recovery, integrated with a reinforced swan neck and including a triport tip having a bezel, and with the handle connected to an ultrasonic generator.

FIG. 2 illustrates the device of FIG. 1 constructed to be connected to a pressure equalizer and to a vacuum, with the fluid passageways shown in dash lines.

FIG. 3 is a longitudinal partially exploded view of an embodiment of a liposuction device utilizing a separate swan neck and a removable shaft tip.

FIG. 4 illustrates an embodiment of a metal memory wire to be used in a hollow cannula shaft of high flexibility and low memory.

FIG. 5 illustrates the embodiment of FIG. 4 with the metal shaft having an increased thickness at the proximal end, and may be of a thin solid material or a thick hollow material.

DETAILED DESCRIPTION OF THE INVENTION

Figure 6:
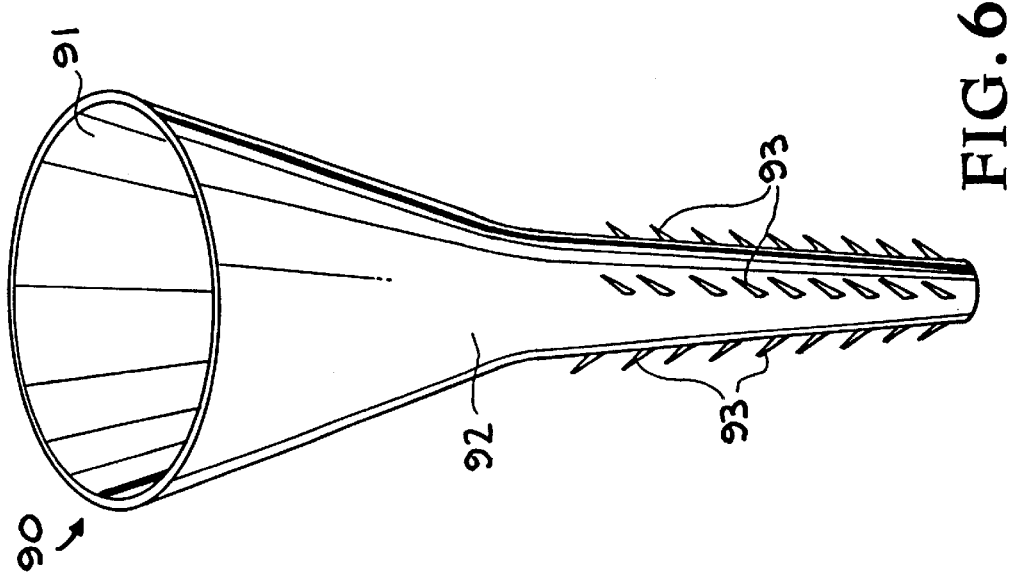
Figure 10:
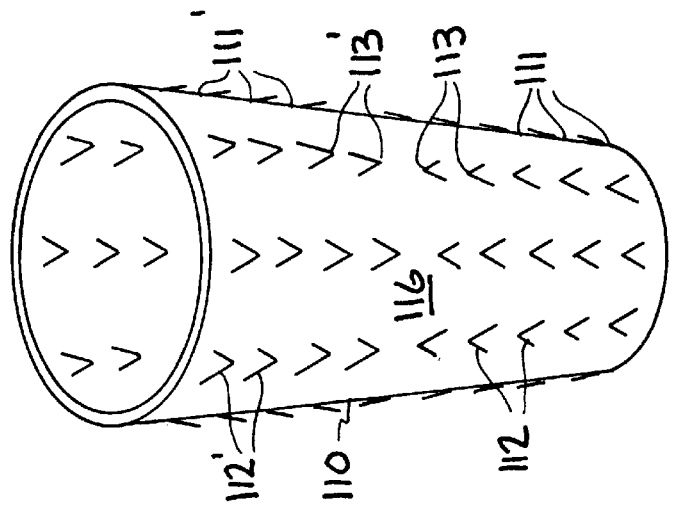
FIG. 10 illustrates another embodiment of the surgical anti-friction device with a plurality of rows of oppositely directed V-shaped cuts defining a space or blank area therebetween.
Figure 9:
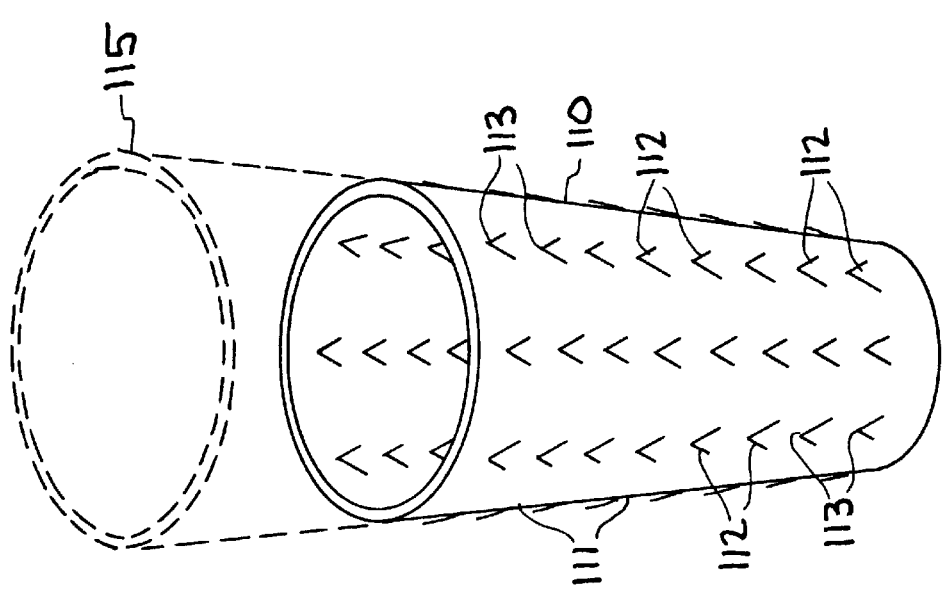
FIG. 9 illustrates another embodiment of the surgical anti-friction device with all rows of V-shaped cuts extending in the same direction.

The present invention is directed to a surgical antifriction device or insert which constitutes an improvement over the entrance wound insert of above referenced copending application Ser. No. 09/203,413, illustrated in FIGS. 6 and 7. The surgical anti-friction device of this invention is designed for use of cannulas for liposuction applications but may be configured to enable use with other surgical tools. In the present invention, the device or insert includes one or more rows of V-shaped cuts with the point extending outwardly and with the rows of cuts extending around the device. In certain embodiments, the rows of V-shaped cuts extend in opposing directions and form a blank space between the rows, which is adapted to be located adjacent the skin of an incision. As can be readily recognized, the oppositely extending rows of V-shaped cuts function to prevent movement of the device or insert in either direction. The length of the device can be extended as needed, as illustrated by the dash lines in FIG. 9. Also, the device may have various configurations including a tapering surface, as shown in FIGS. 8–10, a funnel shape as shown in FIG. 6, or a cylindrical shape to enable insertion of larger surgical tools. The device may be constructed of an anti-friction material or coated with a material, such as TEFLON.

The V-shaped cuts may vary in number from 1 to 1,000, for example, with a size from 0.5 mm to the maximum cutable in a surface of the tapered or cone-shaped device. The cuts may be flush or heat curled. The device or cone may have a superior (larger) opening varying from 3–15 mm and an interior (smaller) opening varying from 1–15 mm for liposuction applications. The principle of the surgical device operates on internal friction downward and external friction upward due to collagen fibers catching on the V-shaped cuts. The transition zone between upwardly extending cuts and downwardly extending cuts is usually where the device settles in the incision. Also, extra width at the top of the device decreases the tendency to penetrate too far into the incision. The device can be made of heat shrinkable TEFLON or plastics, PVC, CPC, gelatin, protein or polymeric sugars. For example, the device may be made by forming a cone shaped mandrel, coating TEFLON on the mandrel, firing, removing the formed cone, and using scissors or cutting die from the V-shaped cuts. Possible uses for the surgical anti-friction device or insert include catheter feed, liposuction cannulas, endoscope (5–30 mm) wound protection, or surgery hole protector, with sizes varying for different procedures from 1–80 mm).

The present invention is particularly adapted for use with highly flexible, reinforced, swan neck liposuction cannulas that, depending on the diameter of the cannula shaft, can be constructed of a metal or a plastic, as described in above referenced copending application Ser. No. 09/203,413. Long metal cannula shafts having a diameter of up to about 3.5 mm have some flexibility and can be effectively utilized for various liposuction procedures, but metal cannula shafts above a diameter of about 3.5 mm have insufficient non-breaking flexibility and thus long plastic cannula shafts made in accordance with the invention of U.S. Pat. No. 6,090,121 having an internal memory wire and having diameters of up to about 6 mm can be effectively utilized.

This plastic/memory wire system allows controlled rigidity of the plastic shafts; the cannulas can be bent into a semi-circle without breaking and yet still return to the original shape. Importantly, the plastic shafts must withstand repeated autoclaving without being deformed or losing their desirable properties. Additionally, the shafts needed to be internally reinforced as extensive testing in vivo without reinforcement demonstrated a need for a graded strength along the shaft in more fibrous liposuction patients and locations. The reinforcing "memory" wires are specially made to be slightly less flexible in the proximal portions of the shaft and more flexible toward the distal tip, thus allowing a convenient gradation of shaft flexibility. A reinforced swan neck disconnect system is used with any number of different plastic shaft diameters, significantly lowering the cost per unit. The wide range of modified plastic shaft performance makes it possible to predictably suction the mid-lower back from an incision in the umbilicus without rotating the patient, as was previously necessary.

Predictable flexibility and excellent memory are imperatives for the metal and plastic shafts. In this system, it is not preferred that the surgeon should be able to bend a cannula prior to placement into the patient and have the cannula maintain the bent shape. Surgeons that desire this quality may find it available in preexisting systems that eventually weaken and require replacement of the cannulas secondary to stress fractures. Also, routine bending by hand is not smooth, regular or uniform, but bumpy.

The benefits of increased flexibility and "memory" can be demonstrated in at least two noteworthy behaviors of the new cannula system. The first, called "opposing motion", occurs if less than one-half of the cannula shaft length has been introduced into the patient, then forcing or pointing the cannula handle to the right will move the cannula tip to the left in the patient and visa versa. Lifting the handle will usually direct the tip downward deeper into the patient's subcutaneous tissue. Second, the cannula tip and distal shaft can be made to ricochet (in conjunction with the aforementioned "opposing motion action" exerted by the cannula handle) within subcutaneous fat of the patient.

Figure 7:
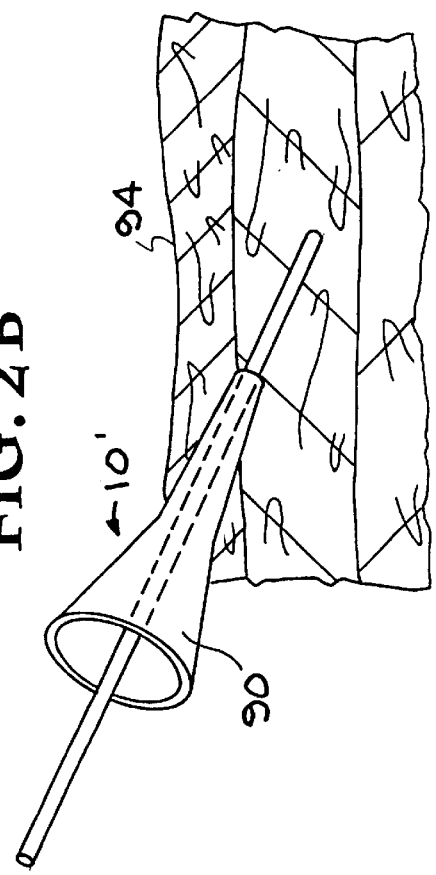
FIGS. 6–7 illustrate an embodiment of an anti-friction insert adapted for insertion into an incision, as shown in FIG. 7.
Figure 8:
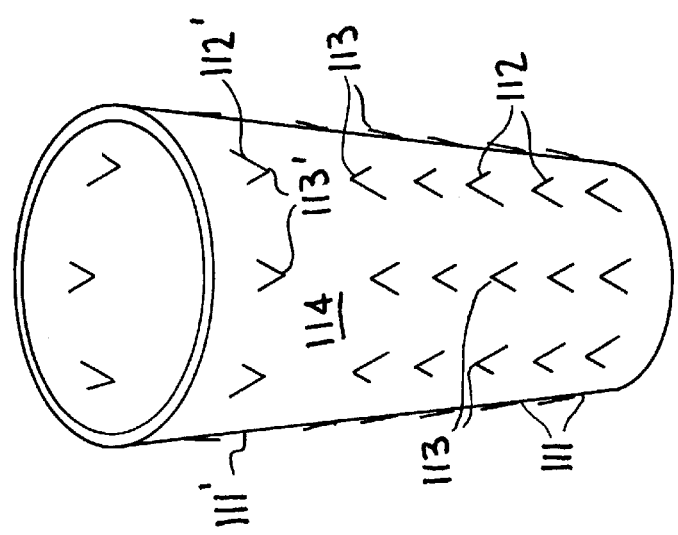
FIG. 8 illustrates an embodiment of the surgical anti-friction device of the present invention having rows of V-shaped cuts, with the upper row extending in an opposite direction and spaced from the adjacent row.

Aside from coating the external portion of cannula shafts with non-stick polymers (that eventually wear off) and applying lubricating jellies to the entrance wounds, another solution to the entrance wound friction problem is the use of temporary intraoperative plastic stents or anti-friction means (such as shown in FIGS. 6–7). Unfortunately, previously available screw-in devices are of thicker materials and damage skin entrance wounds via pressure more than the anti-friction means hereinafter. The preferred anti-friction means is a conical Teflon. The insert is of low friction inside (to aid in cannula passage) and higher friction outside (to reduce the tendency to extrude on cannula backstroke) and can be easily and quickly applied to or removed from any size liposuction entrance wound. Outside friction is increased predictably as a result of projections, unidirectional notches or slits in the insertional exterior portion of the anti-friction means. The non-insertional portion of the anti-friction means may have a single row of oppositely directed notches or slits to prevent over insertion of the device. It has been found that by the use of simple V-shaped cuts, as shown in FIGS. 8–10, the surgical anti-friction device of this invention provides significant advantages over that of the prior known devices.

Figure 2A:
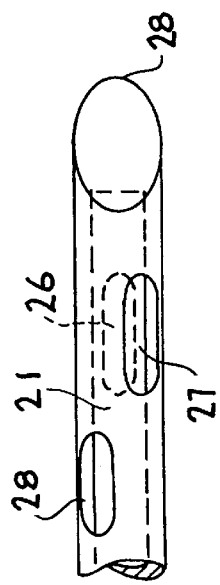
FIG. 2A is a partial top view of an embodiment of the multiport tip of FIGS. 1 and 2.
Figure 2B:
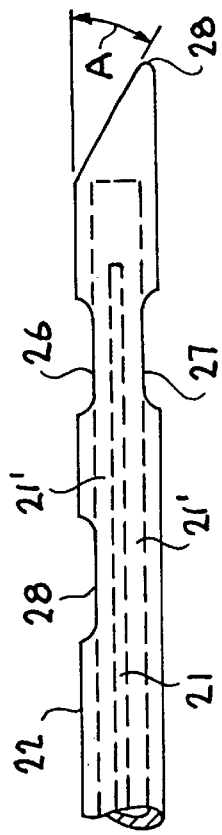
FIG. 2B is a partial side view of the multiport tip of FIG. 2A illustrating the fluid passageways in dashed lines.

Referring now to the drawings, FIGS. 1, 2, 2A and 2B illustrate an embodiment of a liposuction device (generally indicated 10 at 10) which includes a handle or handpiece (generally indicated at 11) and an integral reinforced swan neck/cannula shaft (generally indicated at 12) with the cannula shaft having a tip section (generally indicated at 13). As shown in FIGS. 1 and 2, the handpiece 11 is connected to an ultrasonic generator 14 via a coupling 15, to a fluid supply (such as N2 gas) via a connection tube 16, and a vacuum source via a connection tube 17. As shown in dash lines in FIGS. 2 and 2B, the handpiece 11 includes a channel or tube 18 connected to a channel or tube 19 in reinforced swan neck section 20 and channel or tube 21 in cannula shaft section 22 of the reinforced swan neck/cannula shaft for directing fluid material through the handpiece to the tip section 13, which is suctioned out via a channel or tube 19' and a channel or tube 18'. The fluid cooling, aspiration and ultrasonic arrangements for the device 10 are known in the art and further detail is deemed unnecessary. The handpiece 11 also contains a microprocessor 23 located in a channel 23' (shown by dash lines) for controlling fluid passage through the device 10.

The handpiece 11 also includes removable (threaded) end sections 24 and 25 which are connected to the coupling 15 and connection tubes 16 and 17 and to the reinforced swan neck section 20, the shaft section 22 being fixedly secured in or integrally formed with the reinforced swan neck section 20. The fluid connection 16 is connected to a tube 18 (indicated by dash lines) which extend via a connection to tube 19 in the reinforced swan neck section 20 to the tip section 13 (as seen in FIG. 2B) whereby cooling or cleaning fluids may be introduced at the tip section 13. If desired, the handpiece 11 and swan neck section 20 may be connected by commercially available quick connect assemblies.

Tip section 13 of cannula shaft 22 is of a triport type with a beveled end or bezel. As seen more clearly in FIGS. 2A and 2B, the tip section includes a pair of openings 26 and 27 and a third opening 28 spaced from openings 26 and 27, and a tapered or beveled end or bezel 29 having an angle (,A,) of inclination of about 20 to 60 degrees, preferably about 35 degrees.

The swan neck section 20 is reinforced for several reasons. Reinforcement provides the needed stability to help a surgeon increase leverage on the cannula shaft section 22 and to use it as a guide in combination with the wound opening. The reinforcement may consist of a flexible thickening material (such as thermoplastic or thermoset polymers) or a wire reinforcement or a metallic sleeve or jacket cannula. Preferably, the reinforcement comprises a thickening. The shaft is constructed of a material having excellent flexibility and memory characteristics. Metals and plastics are suitable materials of construction. Examples of plastic material include olefin polymers, fluorocarbon polymers and synthetic rubbers. Preferably polypropylene, polyethylene and tetrafluoroethylene, and more preferably high density polyethylene, are utilized. Examples of suitable metals include aluminum, cold rolled steel, stainless steel, titanium or a titanium alloy.

As pointed out above, the cannula shaft section 22 is constructed of metal (such as stainless steel or non-oxidizing alloys) with a diameter of about 2.0–3.5 mm and up to about 5.0 mm. The shaft section 22 is sufficiently rigid to permit repeated and controlled advancing strokes through the tissue but is sufficiently flexible to enable an amount of bending. The reinforced swan neck section 20 allows for longer insertional lengths of the shaft section 22 (which range from about 15 cm to about 35 cm, and preferably from 25–33 cm). The excised tissue from the surgical site is aspirated via channels 21', 19' and 18' to a vacuum line 17 and to a collection means (not shown). Irrigating fluid (such as saline, antiseptic, anesthetic solutions, hyaluronidase, heparin and epinephrine) or cooling fluid such as an inert gas (nitrogen, for example) are directed through tube 16 and channels 18, 19 and 21 to tip section 13, and are aspirated out with the removed fatty tissue FIG. 3 illustrates an embodiment of a liposuction device wherein the cannula shaft is removably connected to the swan neck, the swan neck is removably connected to the handpiece, and the tip is removably connected to the cannula shaft. As shown, the device (generally indicated at 30) basically includes a handpiece 31, a swan neck 32, a cannula shaft 33 and a triport beveled tip 34. Handpiece 31 includes removable end 35 and 36, with a microprocessor 37 mounted in end 36. Shaft 33 is provided at each end 38 and 39 with internal threads that cooperate with threaded end 40 of swan neck 32 and threaded end 41 of tip 34. A pair of O-ring seals 42 and 43 are located about threaded ends 40 and 41. While not shown, swan neck 32 is threadedly connected at 44 to removable end 36 of handpiece 31 in a similar manner. Tip 34 includes a beveled end 45 and three openings (as in FIGS. 2A–2B) with only two openings shown (46 and 48). The cannula shaft 33 and tip 34 is preferably made of metal if the diameter is less than about 3.5 mm, or made of plastic if the diameter is greater than about 3.5 mm.

If the cannula shaft of FIG. 3 is constructed of plastic with a diameter greater than about 3.5 mm, a flexible metal guide shaft or memory wire (as shown in FIG. 4) is located internally to provide memory for the plastic shaft (to return it to its original shape after bending). Components of FIG. 4 corresponding to FIG. 3 are given corresponding reference numerals. As seen in FIG. 4, a memory wire or guide shaft 50 is secured in an opening 51 of the threaded end 40 of swan neck 32, with wire 50 being of a smaller diameter than the inner diameter opening 51 of end 40 to allow passage of fluids and/or aspiration of fatty tissue to pass therebetween, or the memory wire 50 may be made hollow to provide an aspiration path.

To enable the plastic cannula shaft to bend up to a semi-circle and return to its original position, it is preferred that the memory wire or guide shaft of FIG. 4 have a thicker proximal end than distal end. FIG. 5 illustrates an embodiment wherein the proximal end 52 of the wire 50 of FIG. 4 is provided with a metallic coating 53. If desired, the wire 50 may be tapered or contain tapered sections which decrease from the proximal end 52 to the distal end 54.

FIG. 6 illustrates an embodiment of an anti-friction insert adapted to be inserted into an incision (as shown in FIG. 7). The insert (generally indicated at 90) comprises a funnel shaped member 91 having a lower section 92 provided with a plurality of protruding members 93 which extend at an angle with respect to section 92 which (as shown in FIG. 7) function to prevent the insert 90 from being pulled from an incision in an area of fatty tissue 94 when a liposuction device 10' (such as shown in FIGS. 1–2B and 3) is maneuvered to remove fatty tissue or is withdrawn from insert 90.

FIGS. 8, 9 and 10 illustrate embodiments of the surgical anti-friction device or insert of the present invention, which basically involves the use of V-shaped cuts in the surface of an insert or cone which function to prevent movement of the insert or cone once inserted into an incision or opening. As shown, the embodiments of the surgical device define a hollow cone or tapered hollow member 110, with rows 111 of V-shaped cuts 112 with points 113 extending around the cone 110. As shown in FIG. 8, rows 111 with V-shaped cuts 112 and a single row 111' of V-shaped cuts 112' are in a spaced relationship, and with points 113' the V-shaped cuts 112' extend in a direction opposite to the points 113 of cuts 112 and form a space or area 114 between rows 111 and 111'.

In FIG. 9, the points 113 of V-shaped cuts 112 extend in the same direction in each of the rows 111, with cone 110 being illustrated as being increasable in length by dash lines 115. In FIG. 10, a number of rows 111 and 111' of oppositely directed V-shaped cuts 112 and 112' of the device form a central space or area 116 on the cone or tapered member 110. Thus, as in the FIG. 8 embodiment, the space or area may be located at the skin area when the device or cone 110 is inserted into an incision, such as shown in FIG. 7.

It has thus been shown that the present invention provides a simple constructed surgical anti-friction device or insert using V-shaped cuts which can be easily fabricated from various materials of various sizes and configurations. The location and direction of the V-shaped cuts enable more accurate positioning as well as retaining of the device in an incision or opening. The surgical anti-friction device or insert prevents damage to the incision area by surgical tools therethrough. While the device of the invention has been described for surgical applications, it may be utilized in non-surgical applications wherein an opening can be damaged by repeated movement of tools, etc. therethrough.

While particular embodiments, materials, parameters, etc. have been described and/or illustrated to exemplify and teach the principles of the invention, such are not intended to be limiting. Modifications and changes may become apparent to those skilled in the art, and it is intended that the invention be limited only by the scope of the appended claims.

What is claimed is:

1. A device for insertion into an incision or opening and through which an instrument is adapted to pass, comprising:

a hollow member having a longitudinal axis and having a tapered cone configuration, said hollow member having a plurality of spaced circular rows of spaced V-shaped cuts extending through said hollow member forming a plurality of circular rows of outwardly protruding spaced V-shaped points extending around said hollow member for preventing accidental removal of said hollow from an incision or opening, each of said spaced circular rows of V-shaped cuts lying in a plane which is perpendicular to the longitudinal axis of the hollow member.

2. The device of claim 1, wherein said plurality of spaced V-shaped cuts are positioned in spaced circular rows about said hollow member with at least two rows containing said spaced V-shaped cuts with oppositely directed points.

3. The device of claim 1, wherein said plurality of circular rows include at least two pair of rows of said outwardly extending spaced V-shaped points extending in opposed directions.

4. The device of claim 3, wherein said two pairs of rows are positioned to form a space therebetween having no V-shaped cuts therein.

5. A surgical anti-friction device through which a tool is adapted to pass, comprising:

a hollow member having a longitudinal axis and having a conical configuration, and a plurality of spaced circular rows of spaced V-shaped cuts extending through said hollow member and forming circular rows of outwardly extending spaced points, each of said spaced circular rows of spaced V-shaped cuts lying in a plane which is perpendicular to the longitudinal axis of the hollow member.

6. The device of claim 5, wherein said plurality of spaced circular rows include at least two pair of rows of spaced V-shaped cuts having points which extend in opposing directions to each other, and wherein said two pair of rows form a space therebetween.

7. The device of claim 6, wherein said two pair of rows are located on said hollow member in a spaced relationship.

8. The device of claim 5, wherein said hollow member is constructed of an anti-friction material selected from the group consisting of TEFLON, plastic, PVC, CFC, gelatin, protein, and polymeric sugars.

9. The device of claim 5, wherein said V-shaped cuts are of a size ranging from 0.5 mm and above, and wherein said hollow member is of a tapered configuration having one end with a diameter varying in the range of 3–15 mm and another end having a diameter varying in the range of 1–15 mm.

* * * * *